United States Patent
Feugnet et al.

(10) Patent No.: US 10,570,337 B2
(45) Date of Patent: Feb. 25, 2020

(54) PROCESS FOR PRODUCING BTX AND ALCOHOLS BY CATALYTIC PYROLYSIS OF BIOMASS AND FERMENTATION OF THE GASEOUS PYROLYSIS EFFLUENT

(71) Applicant: IFP Energies nouvelles, Rueil-Malmaison (FR)

(72) Inventors: Frederic Feugnet, Lyons (FR); Nicolas Lopes Ferreira, Croisilles (FR); Slavik Kasztelan, Lyons (FR)

(73) Assignee: IFP Energies nouvelles, Rueil-Malmaison (FR)

(*) Notice: Subject to any disclaimer, the term of this patent is extended or adjusted under 35 U.S.C. 154(b) by 0 days.

(21) Appl. No.: 16/306,086

(22) PCT Filed: May 3, 2017

(86) PCT No.: PCT/EP2017/060547
§ 371 (c)(1),
(2) Date: Nov. 30, 2018

(87) PCT Pub. No.: WO2017/207200
PCT Pub. Date: Dec. 7, 2017

(65) Prior Publication Data
US 2019/0136138 A1 May 9, 2019

(30) Foreign Application Priority Data
May 31, 2016 (FR) .................................... 16 54895

(51) Int. Cl.
*C10G 1/00* (2006.01)
*C10B 53/02* (2006.01)
(Continued)

(52) U.S. Cl.
CPC ............. *C10B 53/02* (2013.01); *B01D 3/14* (2013.01); *B01J 29/40* (2013.01); *C10B 57/06* (2013.01);
(Continued)

(58) Field of Classification Search
CPC ........... C07C 1/22; C07C 29/15; C07C 29/20; C07C 2/66; C07C 2/864; C07C 37/50;
(Continued)

(56) References Cited

U.S. PATENT DOCUMENTS

| | | |
|---|---|---|
| 9,873,836 B2 * | 1/2018 | Blommel .............. C10G 1/002 |
| 2014/0107306 A1 | 4/2014 | Mazanec et al. |
| 2014/0134686 A1 * | 5/2014 | Schultz .................... C12P 7/54 435/140 |

OTHER PUBLICATIONS

Torren R Carlson Et Al: aromatic Production From Catalytic Fast Pyrolysis of Biomass-derived Feedstocks Topics in Catalysis, Kluwer Academic Publishers-Plenum Publishers, NE, vol. 52, No. 3, Jan. 14, 2009 (Jan. 14, 2009), pp. 241-252, XP019689593, ISSN: 1572-9028 019689593.
(Continued)

*Primary Examiner* — Sharon Pregler
(74) *Attorney, Agent, or Firm* — Millen White Zelano and Branigan, PC; Csaba Henter

(57) ABSTRACT

A process is described for producing BTX and alcohols from biomass, by a) catalytic pyrolysis of the biomass in a fluidized-bed reactor producing a gaseous pyrolysis effluent; b) separation of said gaseous pyrolysis effluent into at least one BTX fraction and a gaseous effluent containing at least carbon monoxide and carbon dioxide, c) sending all of the gaseous effluent from separation b) into fermentation producing a liquid fermentation stream containing at least one stream containing at least one oxygenated compound chosen from alcohols, diols, acid alcohols, carboxylic acids, aldehydes, ketones and esters, d) separating the fermentation
(Continued)

stream obtained on conclusion of c) into at least the stream containing at least one oxygenated compound, an aqueous fraction, and an unreacted gaseous effluent, e) recycling at least part of unreacted gaseous effluent into the catalytic pyrolysis a).

14 Claims, 1 Drawing Sheet

(51) Int. Cl.
| | |
|---|---|
| B01J 29/40 | (2006.01) |
| C10G 1/08 | (2006.01) |
| C10B 57/06 | (2006.01) |
| C12P 5/00 | (2006.01) |
| C12P 7/06 | (2006.01) |
| C12P 7/16 | (2006.01) |
| C12P 7/02 | (2006.01) |
| C12P 7/52 | (2006.01) |
| C12P 7/40 | (2006.01) |
| C12P 7/18 | (2006.01) |
| C12P 7/56 | (2006.01) |
| C12P 7/26 | (2006.01) |
| C12P 7/54 | (2006.01) |
| B01D 3/14 | (2006.01) |
| C12P 7/24 | (2006.01) |
| B01J 29/08 | (2006.01) |

(52) U.S. Cl.
CPC ............ *C10G 1/002* (2013.01); *C10G 1/086* (2013.01); *C12P 5/005* (2013.01); *C12P 7/02* (2013.01); *C12P 7/065* (2013.01); *C12P 7/16* (2013.01); *C12P 7/18* (2013.01); *C12P 7/24* (2013.01); *C12P 7/26* (2013.01); *C12P 7/40* (2013.01); *C12P 7/52* (2013.01); *C12P 7/54* (2013.01); *C12P 7/56* (2013.01); *B01D 2257/50* (2013.01); *B01J 29/08* (2013.01); *Y02E 50/10* (2013.01); *Y02E 50/14* (2013.01); *Y02E 50/17* (2013.01)

(58) Field of Classification Search
CPC ......... C07C 37/58; C07C 37/68; C07C 45/78; C07C 51/42; C07C 5/10; C07C 5/333; C10G 1/002; C10G 2400/30; C10G 2300/1011; C10G 1/086; C10G 1/00; C10G 1/02; C10G 2300/1014; C10G 2/32; C10G 2400/02; C10G 2400/04; C10G 2400/08; C10G 3/46; C10G 47/00; C10G 65/02; C10G 65/12
See application file for complete search history.

(56) References Cited

OTHER PUBLICATIONS

Yu-ting Cheng Et Al: production of Renewable Aromatic Compounds by Catalytic Fast Pyrolysis of Lignocellulosic Biomass With Bifunctional Ga/zsm-5 Catalysts Angewandte Chemie International Edition, vol. 51, No. 6, Dec. 27, 2011 (Dec. 27, 2011), pp. 1387-1390, XP055068876, ISSN: 1433-7851, DOI: 10.1002/anie. 201107390055068876.
International Search Report PCT/EP2017/060547 dated Jun. 20, 2017 (pp. 1-6).

* cited by examiner

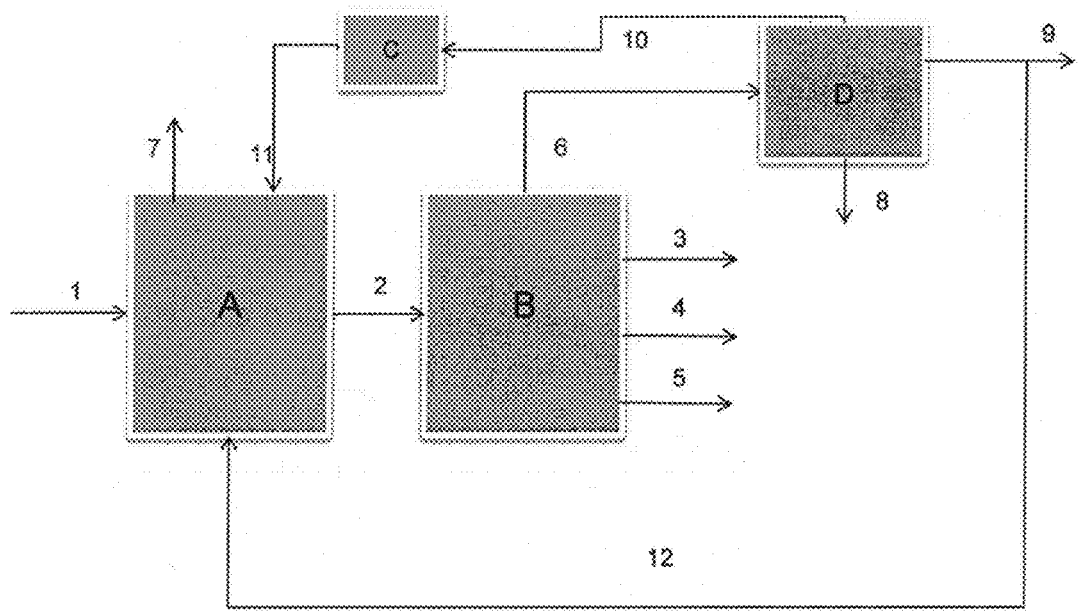

PROCESS FOR PRODUCING BTX AND ALCOHOLS BY CATALYTIC PYROLYSIS OF BIOMASS AND FERMENTATION OF THE GASEOUS PYROLYSIS EFFLUENT

TECHNICAL FIELD

Chemical intermediates are normally produced from fossil resources such as petroleum, natural gas or coal in multi-step processes. In order to replace or supplement the production of chemical intermediates from fossil resources, it is necessary to develop processes for treating non-fossil feedstocks, namely biomass. The present invention relates to a process for producing chemical intermediates and/or bases for fuel and in particular BTX and alcohols from biomass.

PRIOR ART

U.S. Pat. No. 8,277,643 describes a process for producing aromatics, biofuel and olefins by catalytic pyrolysis of biomass in the presence of a zeolite catalyst such as ZSM-5. The process is performed at a temperature at least greater than 300° C., at a pressure of between 1 and 4 atm, at a WHSV of between 0.01 and 10 h$^{-1}$. The process is also characterized by a residence time of the biomass in the reactor of between 2 seconds and 5 minutes.

Patent application WO 2009/111 026 more precisely describes the type of catalyst that can be used in the catalytic pyrolysis step and in particular zeolite catalysts that can be doped with iron, gallium or zinc.

Patent application WO 2011/031 320 describes a process for producing aromatics, biofuel and olefins by catalytic pyrolysis of biomass in the presence of a zeolite catalyst, in which the products obtained by pyrolysis are separated so as to obtain a fraction comprising olefins that is then recycled into the pyrolysis reactor.

Thus, the applicant discovered that by employing a process for producing a BTX fraction by catalytic pyrolysis of lignocellulosic biomass in the presence of a stream of specific oxygenated compounds it was possible to obtain an improved yield of BTX relative to the processes of the prior art.

SUMMARY AND BENEFITS OF THE INVENTION

The invention relates to a process for producing BTX and alcohols from biomass, comprising at least the following steps:
a) catalytic pyrolysis of said biomass in a fluidized-bed reactor producing a gaseous pyrolysis effluent,
b) separation of said gaseous pyrolysis effluent into at least one BTX fraction and a gaseous effluent comprising at least carbon monoxide and carbon dioxide,
c) sending all of the gaseous effluent comprising at least carbon monoxide and carbon dioxide derived from the separation step b) into a fermentation step producing a liquid fermentation stream comprising at least one stream comprising at least one oxygenated compound chosen from alcohols containing 2 to 6 carbon atoms, diols containing 2 to 4 carbon atoms, acid alcohols containing 2 to 4 carbon atoms, carboxylic acids containing 2 to 6 carbon atoms, aldehydes containing 2 to 12 carbon atoms, ketones containing 3 to 12 carbon atoms and esters containing 2 to 12 carbon atoms, alone or as a mixture,
d) separating said fermentation stream obtained on conclusion of step c) into at least said stream comprising at least one oxygenated compound, an aqueous fraction and an unreacted gaseous effluent,
e) recycling at least part of said unreacted gaseous effluent into the catalytic pyrolysis step a).

Throughout the rest of the text, the term "BTX cut" means a fraction comprising a mixture of benzene, toluene and xylenes (ortho, meta, para).

One advantage of the present invention is thus that of providing a process for simultaneously producing BTX and oxygenated compounds and in particular alcohols, from biomass, making it possible to obtain an improved yield of BTX relative to the prior art, by performing a step of catalytic pyrolysis of biomass coupled with a step of fermentation of all the gaseous effluent comprising CO and $CO_2$ produced and separated out after the catalytic pyrolysis step.

Another advantage of the present invention lies in the fact that the unreacted uncondensable gaseous effluent in the fermentation step which is separated from the liquid fermentation stream obtained and recycled into the catalytic pyrolysis step has a higher partial pressure of hydrocarbon than that in the prior art, which makes it possible to improve the production of BTX in the catalytic pyrolysis step.

Another advantage of a preferred embodiment of the present invention is therefore that of providing a process for simultaneously producing a BTX cut and a stream of oxygenated compounds and preferably of alcohols such as ethanol and/or butanol, at least part of said stream of oxygenated compounds produced by fermentation being used to increase the yield of BTX, thus increasing the flexibility of the process according to the invention.

Another advantage of the present invention also lies in the optimization of the upgrading of the carbon derived from biomass, in particular as chemical intermediates such as BTX, but also as bases for biofuel and as high value-added bioalcohol.

Another advantage of the present invention is that of providing an optimized process for producing a BTX cut, in that the gaseous effluent comprising CO and $CO_2$ produced by catalytic pyrolysis and used as feed for the fermentation step is withdrawn from the catalytic pyrolysis step at a temperature and a pressure that are compatible with its direct use in a fermentation step, without an intermediate compression step. The gaseous effluent comprising CO and $CO_2$ produced by catalytic pyrolysis also has a composition that is compatible with its use in a fermentation step.

DETAILED DESCRIPTION OF THE INVENTION

In accordance with the invention, the process for producing BTX and alcohols from biomass includes a step a) of catalytic pyrolysis of said biomass in a fluidized-bed reactor producing a gaseous pyrolysis effluent.

Step a) of Catalytic Pyrolysis

Examples of fluidized-bed reactors may be found in Howard, R. J. (1989). "Principles of fluidized-bed technology and applications." New York, Adam Higler of N.Y.; Tavoulareas, S. (1991) Combustion Technology. Annual Reviews Inc16, 25-27, and Trambouze, P., and Euzen, J. (2004). "Chemical reactors: From design to operation." (R. Bonormo, Trans.). Paris: Editions Technip.

The fluidized-bed reactor used in the process according to the invention preferably operates in turbulent conditions, i.e. in a surface gas velocity range of between 0.5 and 0.8 m/s.

The term "surface gas velocity" means the volume flow rate of gas referred to the surface area of the reactor.

This turbulent-bed application is favoured over the so-called "riser" technology usually employed for FCC, in that there are high yields of coke and of incompletely converted biomass usually called "char" in FCC technology, and consequently there is a high concentration of coke on the catalyst. By virtue of the proposed application, the heat balance of the catalytic pyrolysis step is decoupled by regulating the residence time of the catalyst in the reactor via the rate of withdrawal of the latter to the regenerator, thus making it possible to limit the percentage of coke on the catalyst and therefore limit the temperature of the regenerator within an operable range.

According to the invention, the feedstock used in the present invention is biomass. Preferably, the feedstock is lignocellulosic biomass or one or more constituents of lignocellulosic biomass chosen from the group comprising cellulose, hemicellulose and/or lignin.

Lignocellulosic biomass may consist of wood, agricultural waste or vegetable waste. Other non-limiting examples of lignocellulosic biomass material are farm residues (straw, maize stover, etc.), forestry residues (products from first thinning), forestry products, dedicated crops (short rotation coppice), food industry residues, organic household waste, waste from woodworking plants, wood used in construction, paper, whether or not recycled. Lignocellulosic biomass may also come from by-products of the papermaking industry such as Kraft lignin, or black liquors from the manufacture of paper pulp.

The lignocellulosic biomass may advantageously undergo at least one step of pretreatment before it is fed into the process according to the invention. Preferably, the biomass is ground and dried, until the desired granulometry is obtained. A feed having a particle diameter between 0.3 and 0.5 mm may advantageously be obtained. Typically, the particle size of the lignocellulosic biomass for pyrolysis is a sufficient particle size to pass through a 1-mm screen up to a sufficient particle size to pass through a 30-mm screen.

Preferably, the biomass for pyrolysis is advantageously fed into a compartment for pneumatic entrainment or transport so as to be entrained into the fluidized bed by an entraining fluid. Preferably, the entraining fluid used is gaseous nitrogen. However, it is also envisaged that other non-oxidizing entraining fluids may be used. Preferably, the pyrolysis gas produced during the process may be recycled and used as entraining fluid. Said pyrolysis gas is mainly constituted of an uncondensable gaseous effluent, comprising at least carbon monoxide (CO) and carbon dioxide ($CO_2$), and also advantageously comprising light olefins comprising from 2 to 4 carbon atoms, produced during step a). In this way, the cost of performing pyrolysis can be reduced considerably. The biomass may be loaded into a feed hopper or some other device for feeding the biomass into the entrainment compartment in a suitable amount. In this way, a constant amount of biomass is delivered into the entrainment compartment.

The entraining fluid advantageously transports the biomass from the entrainment compartment into the fluidized bed through a feed tube. Typically, the feed tube is cooled to maintain the temperature of the biomass at a required level before it enters the fluidized bed. The feed tube may be cooled by jacketing the tube, typically with an air-cooled or liquid-cooled jacket. However, it is also envisaged that the feed tube is not cooled.

According to the invention, the catalytic pyrolysis step a) operates in the presence of a catalyst. Preferably, said step a) operates in the presence of a zeolite catalyst comprising and preferably constituted of at least one zeolite chosen from ZSM-5, ferrierite, zeolite beta, zeolite Y, mordenite, ZSM-23, ZSM-57, EU-1 and ZSM-11, and preferably the catalyst is a catalyst comprising only ZSM-5. The zeolite used in the catalyst employed in the catalytic pyrolysis step a) may advantageously be doped, preferably with a metal chosen from iron, gallium, zinc and lanthanum.

Depending on the catalyst used and the desired reaction products, the temperature employed in the catalytic pyrolysis step a) may be adjusted. In certain embodiments, the catalytic pyrolysis step is performed at a temperature between 400 and 1000° C., preferably between 400 and 650° C., preferably between 450 and 600° C. and preferably between 450 and 590° C. In particular, it is the catalyst obtained from the regeneration step that makes it possible to provide these temperature ranges of the reactor. The pyrolysis step a) is also advantageously performed at an absolute pressure between 0.1 and 0.5 MPa and at a WHSV between 0.01 and 10 $h^{-1}$, preferably between 0.01 and 5 $h^{-1}$, preferably between 0.1 and 3 $h^{-1}$ and very preferably between 0.1 and 3 $h^{-1}$.

Under these conditions, the biomass will first undergo rapid pyrolysis in the reactor on coming into contact with the hot catalyst obtained from the regenerator, which performs the role of heat carrier in this step. The gases resulting from this pyrolysis will then react on the catalyst, which this time performs its role of catalyst for catalysing the reactions that produce the required chemical intermediates.

In accordance with the invention, the products obtained on conclusion of the catalytic pyrolysis step a) are advantageously recovered in the form of a gaseous pyrolysis effluent comprising at least a portion of the BTX cut.

Separation Step B

In accordance with the invention, the process comprises a step b) of separating said gaseous pyrolysis effluent into at least one BTX fraction and a gaseous effluent comprising at least carbon monoxide (CO) and carbon dioxide ($CO_2$).

Advantageously, besides the liquid BTX fraction and the uncondensable gaseous effluent, comprising at least carbon monoxide (CO) and carbon dioxide ($CO_2$), the separation step b) also makes it possible to separate out a liquid cut predominantly comprising compounds with a number of carbon atoms of greater than 9, i.e. at least 50% by weight of C9+ compounds and water.

Said uncondensable gaseous effluent, comprising at least carbon monoxide (CO) and carbon dioxide ($CO_2$), also advantageously comprises light olefins comprising from 2 to 4 carbon atoms.

The coked catalyst and the unconverted biomass, usually called "char", are advantageously withdrawn from the reactor and preferably sent to a stripper so as to remove the hydrocarbons potentially adsorbed, and thus prevent their combustion in the regenerator, by contacting with a gas chosen from steam, an inert gas such as nitrogen for example and at least a portion of the uncondensable gaseous cut rich in CO and $CO_2$ resulting from fractionation of the gaseous effluent derived from the catalytic pyrolysis step.

Said coked catalyst and the char, optionally stripped, are advantageously sent to a regenerator, where coke and char are burned by adding air or oxygen. The catalyst thus regenerated is advantageously recycled to the reactor of the catalytic pyrolysis step in order to undergo another cycle.

The catalytic pyrolysis step of the process according to the invention allows production of at least 10 wt % and preferably at least 15 wt % of aromatics relative to the total weight of the reaction products obtained, with a selectivity of at least 65% and preferably of at least 70% of BTX.

The process according to the invention comprising at least one step of catalytic pyrolysis of a biomass feed therefore produces a gaseous effluent comprising at least one BTX liquid fraction and a gaseous effluent comprising at least carbon monoxide and carbon dioxide. The process also makes it possible to obtain, in addition to the BTX cut, a heavier liquid fraction, predominantly aromatic, called "C9+ cut", which may advantageously be upgraded in a process external to the process according to the invention.

Fermentation Step C

In accordance with the invention, the process comprises a step of sending all of the gaseous effluent comprising at least carbon monoxide and carbon dioxide derived from the separation step b) into a fermentation step c) producing a liquid fermentation stream comprising at least one stream comprising at least one oxygenated compound chosen from alcohols containing 2 to 6 carbon atoms, diols containing 2 to 4 carbon atoms, acid alcohols containing 2 to 4 carbon atoms, carboxylic acids containing 2 to 6 carbon atoms, aldehydes containing 2 to 12 carbon atoms, ketones containing 3 to 12 carbon atoms and esters containing 2 to 12 carbon atoms, alone or as a mixture, The gaseous effluent comprising at least carbon monoxide and carbon dioxide derived from the separation step b) generally comprises a carbon monoxide (CO) content advantageously between 0.6% and 50% by weight of CO, and preferably between 10% and 40% by mass and a $CO_2$ content of between 0.5% and 40% by mass and preferably between 10% and 30% by mass, the percentages being expressed as mass percentages relative to the total mass of said gaseous effluent.

Moreover, said gaseous effluent also generally comprises hydrogen, C1-C4 light gases, olefins and may also contain a small content of aromatic impurities, for instance benzene and toluene.

The content of aromatic impurities may advantageously be decreased by adjusting the operating conditions of the catalytic pyrolysis step and also the level of recycle returned to the reactor.

The gaseous effluent comprising CO and $CO_2$ produced by catalytic pyrolysis has a composition compatible with its use in a fermentation step.

Moreover, the gaseous effluent comprising at least carbon monoxide and carbon dioxide derived from the separation step b), used as feed for the fermentation step d), is withdrawn from step a) of catalytic pyrolysis at a temperature and a pressure that are compatible with its direct use in a fermentation step. The process according to the invention may require compressing or decompressing said gaseous effluent to allow better functioning of the fermentation step. In a preferred embodiment, the process according to the invention comprises neither a step of compression nor of heating of said gaseous effluent comprising carbon monoxide (CO) and carbon dioxide ($CO_2$) to establish operating conditions that are compatible with a fermentation step.

The gaseous effluent comprising at least carbon monoxide and carbon dioxide derived from the separation step b), used as feed for the fermentation step d), is generally withdrawn at a temperature of between 20 and 60° C. and at a pressure of between 0.1 and 0.5 MPa.

The fermentation step c) is advantageously performed in the presence of at least one microorganism, also known as an acetogenic strain.

In the rest of the text hereinbelow, the terms "fermentation", "fermentation step", or "fermentation reaction" relate to conversion of the gases $H_2$, CO and/or $CO_2$ and include both the growth phase of the fermenting microorganism and the phase of production of the molecules of interest, such as alcohols, acids, acid alcohols and/or carboxylic acids by this microorganism.

In point of fact, the capacity of certain microorganisms to grow on gaseous substrates such as carbon monoxide (CO), carbon dioxide ($CO_2$) and/or hydrogen ($H_2$) as sole source of carbon was discovered in 1903. A large number of anaerobic organisms, more particularly "acetogenic" organisms, have this capacity of metabolizing CO and/or the $CO_2/H_2$ pair to produce various final molecules of interest such as acetate, butyrate, ethanol and/or n-butanol.

The microorganisms capable of performing this fermentation process are mainly from the genus *Clostridium*, but other microorganisms, for instance those from the genera *Acetobacteria, Butyribacterium, Desulfobacterium, Moorella, Oxobacter* or *Eubacteria* may also be used for performing this fermentation process.

The microorganisms are therefore chosen so as to lead to production of the desired products in the fermentation step. The fermentation products may include, for example, alcohols and acids.

For example, various patents describe strains capable of producing the aforementioned products of interest, starting from synthesis gas. Among the acetogenic strains of the genus *Clostridium*, mention may be made of patent U.S. Pat. No. 5,173,429 describing a strain of *Clostridium ljungdahlii* (ATCC 49587) that produces ethanol and acetate. Other strains of the same species are described in WO 2000/68407, EP 117 309 and patents U.S. Pat. Nos. 5,173,429, 5,593,886 and 6,368,819, WO 1998/00558 and WO 2002/08438. Certain strains of *Clostridium* such as the strains of *Clostridium autoethanogenum* (DSM 10061 and DSM 19630) described in WO2007/117 157 and WO 2009/151 342, *Clostridium ragsdalei* (P11, ATCC BAA-622) described in patent U.S. Pat. No. 7,704,723 or *Clostridium carboxidivorans* (ATCC PTA-7827) described in patent application US 2007/0 276 447, are also capable of producing molecules of interest by fermentation starting from gases ($H_2$, CO and/or $CO_2$).

Said acetogenic strain(s) or microorganism(s) used in the fermentation step of the process according to the invention are preferably chosen from the following microorganisms: *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter pacificus subterraneous, hydrogenoformans Carboxydothermus, Clostridium aceticum, Clostridium acetobutylicum, Clostridium acetobutylicum* P262 (DSM 19630 from DSMZ Germany), *Clostridium autoethanogenum* (DSM 19630 from DSMZ Germany), *Clostridium autoethanogenum* (DSM 10061 from DSMZ Germany), *Clostridium autoethanogenum* (DSM 23693 from DSMZ Germany), *Clostridium autoethanogenum* (DSM 24138 from DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium ERI2 ljungdahlii* (ATCC 55380), *Clostridium ljungdahlii* C-01 (ATCC 55988), *Clostridium ljungdahlii* O-52 (ATCC 55889), *Clostridium magnum, Clostridium pasteurianum* (DSM 525 from DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, sulfurreducens Geobacter, Methanosarcina acetivorans, Methanosarcina Barken, Mouella*

*thermoacetica, Mouella the rmoautotrophica, Oxobacter pfennigii, Peptostreptococcus productus, Ruminococcus productus, Thermoanaerobacter kivui*, and mixtures thereof.

Moreover, it should be understood that other microorganisms capable of assimilating $H_2$, CO (otherwise known as carboxidotrophs) and/or $CO_2$ as source of carbon may also be used in step c) of the present invention. All of the aforementioned microorganisms are called anaerobic, i.e. incapable of growing in the presence of oxygen. However, aerobic microorganisms may also be used, such as microorganisms belonging to the species Escherichia coli. For example, one publication has demonstrated that it is possible to produce a strain that is genetically modified to express the genes coding for the enzymes responsible for assimilation of CO (genes of the Wood-Ljungdahl metabolic pathway) in order to produce molecules of interest, such as isopropanol, starting from an important metabolic intermediate: acetyl CoA (Trawick, J. D.; Burk, M. J.; Burgard, A. P. Microorganisms and Methods for Conversion of Syngas and Other Carbon Sources to Useful Products. Patent WO 2010/071 697). Burk, M.; Schilling, C. H.; Burgard, A.; Trawick, J. D. Methods and Organisms for Utilizing Synthesis Gas or Other Gaseous Carbon Sources and Methanol. Patent WO2009/094485). Other genetically modified microorganisms have been described for producing isopropanol, for instance the microorganism *C. ljungdahlii* (US 2012/0 252 083; Lanzatech).

In preferred embodiments, the microorganisms are chosen from *Clostridium autoethanogenum, Clostridium ljungdahlii, Clostridium aceticum, Morella thermoacetica, Acetobacterium woodii* and *Alkalibaculum bacchi* for producing ethanol and/or acetate, *Clostridium autoethanogenum, Clostridium ljungdahlii* and *C. ragdalei* for producing 2,3-butanediol and *Clostridium carboxidivorans, Clostridium drakei, Clostridium scatologenes* or *Butyribacterium methylotrophicum* for producing butyrate and butanol. Cultures comprising a mixture of two or more microorganisms may also be used.

The fermentation step c) may advantageously be performed aerobically or anaerobically and preferably anaerobically.

The fermentation step c) is advantageously performed in one or more reactors or "bioreactors".

The term "bioreactor" comprises a fermentation device consisting of one or more tanks or tubular reactors, comprising the devices of the type CSTR or Continuous Stirred Tank Reactor using the English-language terminology, ICR or Immobilized Cell Reactor using the English-language terminology, TBR or Trickle Bed Reactor, fermenters of the Gas Lift type, bubble columns, or membrane reactor such as the HFMBR system or Hollow Fibre Membrane Bio-Reactor using the English-language terminology, a static mixer, or any other suitable device for gas-liquid contact.

All of the gaseous effluent comprising at least carbon monoxide and carbon dioxide derived from the separation step b), used as feed for the fermentation step c), is fed into the fermentation reactor(s) in the form of a gaseous substrate. Each fermentation reactor contains a culture medium.

Preferably, the required concentration of gaseous substrate (CO, $CO_2$, $H_2$) in the culture medium of said fermentation reactor(s) is at least 2.5 mmol/L of CO and/or $CO_2$. Said gaseous effluent used as feed for the fermentation step c) is fed into the fermentation reactor(s) in the form of a gaseous substrate advantageously containing a CO content of between 0.6% and 50% by weight of CO, and preferably between 10% and 40% by mass and a $CO_2$ content of between 0.5% and 40% by mass and preferably between 10% and 30% by mass, the percentages being expressed as mass percentages relative to the total mass of said gaseous effluent.

The gaseous effluent derived from the separation step b) also advantageously comprises hydrogen, C1-C4 light gases, olefins and may also contain a small content of aromatic impurities, for instance benzene and toluene. The sum of the content of elements composing said effluent is equal to 100%.

According to a preferred embodiment, the fermentation step c) comprises a propagation chain for an acetogenic strain so as to provide a sufficient amount of cells to inoculate one or more main reactors, said propagation chain comprising: i) inoculation of the acetogenic strain in a first propagation reactor providing a minimum density of viable cells for a second propagation reactor having a larger volume, and ii) growth of said acetogenic strain in the second reactor to provide a density of cells adapted to inoculate a third propagation reactor, which is the largest in terms of volume. If necessary, the propagation chain may comprise a larger number of propagation reactors.

The fermentation step also comprises a production step in which the fermentation process is optimal, i.e. in which the molecules of interest are produced in large amount. The stream comprising at least one oxygenated compound as claimed is therefore produced in said production step.

Preferably, the propagation step may be performed in one or more reactors for propagation of the microorganism, all of these reactors being connected to allow transfer of the microbial culture.

One or more "production" reactors in which the fermentation process takes place are also employed.

The microorganisms or acetogenic strains are generally cultured until an optimum cell density is obtained for inoculating the production reactors. This level of inoculum may vary from 0.5 to 75%, which makes it possible to have production reactors that are larger than the propagation reactors. Thus, the propagation reactor can be used for seeding several other larger production reactors.

In the case where the fermentation step comprises a propagation step and a production step, the gaseous effluent comprising carbon monoxide (CO) and carbon dioxide ($CO_2$) may advantageously be introduced in the fermentation step at the level of the reactors of the production step.

At least one additional carbon-based substrate may advantageously be used in combination with the gaseous substrates derived from the separation step b), for growing the microorganisms in the propagation step. Said carbon-based substrate may advantageously be chosen from n-monosaccharides such as glucose, fructose or xylose, polysaccharides such as starch, sucrose, lactose or cellulose, metabolic intermediates such as pyruvate or any other carbon-based substrate known to a person skilled in the art as being assimilable by the microorganisms used in the process. Said carbon-based substrate may also be a mixture of two or more of these carbon-based substrates.

Control of the operating conditions is also necessary for optimizing the execution of the fermentation step. By way of example, Lowe et al. (Microbiological Review, 1993 57: 451-509), or Henstra et al. (Current Opinion in Biotechnology 2007, 18:200-206), summarize the optimum operating conditions in terms of temperatures and pH, for growing the microorganisms that may be used in the fermentation process. The pH is one of the most important factors for the fermentation activity of the microorganisms used in the process. Preferably, said fermentation step d) is performed at a pH of between 3 and 9, preferably between 4 and 8, and more preferably between 5 and 7.5.

Temperature is also an important parameter for improving fermentation as it has an influence both on microbial activity and on the solubility of the gases used as substrate. The choice of temperature depends on the microorganism used, certain strains being capable of growing in moderate temperature conditions (strains called mesophiles) and others in conditions of high temperatures (thermophilic microorganisms). Preferably, said fermentation step c) is performed at a growth temperature between 20 and 80° C. Preferably, said fermentation step c) is performed at a growth temperature between 20 and 40° C. for mesophilic strains and preferably between 25 and 35 and between 40 and 80° C. for thermophilic strains, and preferably between 50 and 60° C.

The oxidation-reduction potential (otherwise known as the "redox" potential) is also an important parameter to be controlled in the fermentation process. The redox potential is preferably below −450 mV and preferably between −150 and −250 mV. Said fermentation step c) is moreover advantageously performed at a pressure of between 0.1 and 0.4 MPa.

The nutrient medium or culture medium of the fermentation step may advantageously contain at least one reducing agent so as to improve the performance of the fermentation process by controlling the redox potential of the fermentation step.

The nutrient medium may also comprise minerals, vitamins, metal co-factors or metals specific to the metalloenzymes involved in the routes for conversion of the gas into products of interest. Anaerobic nutrient media suitable for fermentation of ethanol using CO and/or $CO_2$ as the sole source(s) of carbon are known by a person skilled in the art. For example, suitable media are described in patents U.S. Pat. Nos. 5,173,429 and 5,593,886 and WO 02/08438, WO 2007/115 157 and WO 2008/115 080 or the publication by J. R. Phillips et al. (Bioresource Technology 190 (2015) 114-121).

The composition of the nutrient medium must allow efficient conversion of the gaseous substrate to a molecule of interest. This conversion is advantageously at least 5% and it may be up to 99%, preferably from 10% to 90%, and preferably 40% to 70%.

The nutrient medium may contain at least one or more sources of nitrogen, one or more sources of phosphorus and one or more sources of potassium. The nutrient medium may comprise one of these three compounds, or any combination of the three, and in an important aspect, the medium must comprise all three compounds. The source of nitrogen may be chosen from ammonium chloride, ammonium phosphate, ammonium sulfate, ammonium nitrate, and mixtures thereof. The source of phosphorus may be chosen from phosphoric acid, ammonium phosphate, potassium phosphate, and mixtures thereof. The source of potassium may be chosen from potassium chloride, potassium phosphate, potassium nitrate, potassium sulfate, and mixtures thereof.

The nutrient medium may also comprise one or more metals such as iron, tungsten, nickel, cobalt, magnesium, sulfur and thiamine. The medium may comprise any one of these components or any combination, and in an important aspect it comprises all of these components. The source of iron may be chosen from ferrous chloride, ferrous sulfate and mixtures thereof. The source of tungsten may be chosen from sodium tungstate, calcium tungstate, potassium tungstate and mixtures thereof. The source of nickel may include a source of nickel chosen from the group constituted by nickel chloride, nickel sulfate, nickel nitrate, and mixtures thereof. The source of cobalt may be chosen from cobalt chloride, cobalt fluoride, cobalt bromide, cobalt iodide and mixtures thereof. The source of magnesium may be chosen from magnesium chloride, magnesium sulfate, magnesium phosphate, and mixtures thereof. The source of sulfur may comprise cysteine, sodium sulfide, and mixtures thereof.

The fermentation step c) may also advantageously be performed as described in patent applications WO 2007/117 157, WO 2008/115 080, U.S. Pat. Nos. 6,340,581, 6,136, 577, 5,593,886, 5,807,722 and U.S. 5,821,111.

As mentioned above, the optimum operating conditions for performing this fermentation step depend partly on the microorganism or microorganisms used. The most important parameters to be controlled comprise the pressure, temperature, gas and liquid flow rate, pH of the medium, redox potential, stirring speed and the level of inoculum. It is also necessary to ensure that the contents of gaseous substrates in the liquid phase are not limiting. Examples of suitable operating conditions are described in patents WO 02/08438, WO 07/117 157 and WO 08/115 080. The ratio between the $H_2$ and the gaseous substrates CO and $CO_2$ may also be large to control the nature of the alcohols produced by the fermenting microorganisms. In patent application WO12/131627, it is for example described that depending on the level of hydrogen, it is possible to produce either ethanol alone, or ethanol and 2,3-butanediol if the $H_2$ percentage is below 20% (by volume). The typical composition of the purge gas fed to the production reactors would advantageously make it possible to produce 2,3-butanediol and ethanol by *Clostridium autoethanogenum*.

Preferably, fermentation should be performed at a pressure above the ambient pressure. A pressure above ambient pressure makes it possible to substantially increase the rate of transfer of gas to the liquid phase so that it is assimilated by the microorganism as a carbon source. This operation notably makes it possible to reduce the retention time (defined as the volume of liquid in the bioreactor divided by the flow rate of feed gas) in the bioreactor and therefore to improve productivity (defined as the number of grams of molecules of interest produced per litre and per day of production) of the fermentation process. Examples of productivity improvement are described in patent WO02/08438.

In accordance with the invention, said fermentation step c) produces a liquid fermentation stream comprising at least one stream comprising at least one oxygenated compound chosen from alcohols containing 2 to 6 carbon atoms, diols containing 2 to 4 carbon atoms, acid alcohols containing 2 to 4 carbon atoms, carboxylic acids containing 2 to 6 carbon atoms, aldehydes containing 2 to 12 carbon atoms and preferably 2 to 6 carbon atoms, ketones containing 3 to 12 carbon atoms and preferably 3 to 6 carbon atoms, and esters containing 2 to 12 carbon atoms and preferably 2 to 6 carbon atoms, alone or as a mixture. Preferably, the alcohols containing 2 to 6 carbon atoms are chosen from ethanol, n-propanol, isopropanol, butanol, isobutanol and hexanol, the diols containing 2 to 4 carbon atoms are chosen from 2,3-butylene glycol (2,3-butanediol), the acid alcohol containing 2 to 4 carbon atoms is preferably lactic acid, the carboxylic acids containing 2 to 6 carbon atoms are chosen from acetic acid, propionic acid, butyric acid, pyruvic acid, levulinic acid and hexanoic acid, the aldehydes containing 2 to 12 carbon atoms are chosen from ethanal, propanal, butanal, pentanal, 3-methylbutanal, hexanal, furfural and glyoxal, alone or as a mixture, the ketones containing 3 to 12 carbon atoms and preferably 3 to 6 carbon atoms are chosen from acetone, butanone, cyclohexanone, acetophenone and acetylacetone, alone or as a mixture, and the esters containing 2 to 12 carbon atoms and preferably 2 to 6 carbon atoms are chosen from methyl formate, methyl acetate, methyl propionate, methyl butanoate, methyl pentanoate, ethyl acetate, propyl acetate, isopropyl acetate, butyl acetate, isobutyl acetate and butyl butyrate, alone or as a mixture.

Preferably, the liquid fermentation stream comprises at least one stream comprising at least one oxygenated compound chosen from ethanol, n-propanol, isopropanol, butanol, isobutanol, hexanol, acetic acid, butyric acid, hexanoic acid, lactic acid, acetone, butanone and 2,3-butylene glycol (2,3-butanediol), alone or as a mixture.

Said liquid fermentation stream produced by the fermentation step c) also advantageously contains nutrient medium, molecules of interest (alcohols, alcohol acids, acids), i.e. a stream of oxygenated compounds as described above and bacterial cells.

A hydrogen supplement may advantageously be optionally introduced into said fermentation step c) in the case where the composition of the feed feeding said step does not comprise a sufficient amount of hydrogen. The use of a gaseous substrate lean in $H_2$ leads to production of important acids. In point of fact, as mentioned previously, the hydrogen supplement makes it possible to improve the conversion of the CO present in the fermentation medium into alcohols (according to the balance equations of Bertsch and Müller Biotechnol Biofuels (2015) 8:210: 6 CO→1 ethanol+4 $CO_2$ then 6 $H_2$+2 $CO_2$→1 ethanol+0.3 ATP) and promote the conversion of $CO_2$.

The supplemental hydrogen may advantageously come from any process for producing hydrogen, for instance a steam reforming process or a catalytic reforming process, electrolysis of water, dehydrogenation of alkanes, and its hydrogen purity is usually between 75 vol % and 99.9 vol %.
Separation Step d)

In accordance with the invention, said liquid fermentation stream produced by the fermentation step c) is separated so as to obtain said stream of oxygenated compounds.

The process according to the invention comprises a step d) of separating said fermentation stream obtained on conclusion of step c) into at least said stream comprising at least one oxygenated compound, an aqueous fraction and an unreacted gaseous effluent.

Preferably, the aqueous fraction separated out predominantly comprises water.

Preferably, the unreacted gaseous effluent comprises uncondensable gases and preferably carbon monoxide and carbon dioxide that have not reacted during the fermentation step c). Said separation step is advantageously performed via separation methods known to those skilled in the art.

In a preferred embodiment, the separation step d) may advantageously be performed with steam according to the techniques known to those skilled in the art.

In particular, said separation is advantageously performed using steam originating from the catalytic pyrolysis step a).

The steam may advantageously be generated by combustion of the coke and char in the regenerator and recovered via a hot catalyst cooler or "cat-cooler", using the English-language terminology.

In this embodiment, the energy required for separation is therefore supplied by the catalytic pyrolysis step, which reinforces the synergy between the two steps of the process.

Said stream of oxygenated compounds produced by said fermentation step and separated from said liquid fermentation stream in step d) may also advantageously be separated into different streams comprising said molecules of interest.

As an example, it is possible to recover the various alcohols produced, contained in said stream of oxygenated compounds, by methods such as distillation or fractional evaporation. Examples of techniques of this type comprise those described in WO 2007/117 157, WO 2008/115 080, U.S. Pat. Nos. 6,340,581, 6,136,577, 5,593,886, 5,807,722 and 5,821,111.

Distillation of alcohol from said stream of fermentation liquid derived from said step c) may advantageously be performed after passage through a beer column for obtaining a stream of concentrated alcohols and the optional recycling of the acids and other molecules reassimilable by the microorganism(s) used in said fermentation step. The stream of alcohols may then be treated via various distillation columns allowing selective or non-selective separation of the various alcohols present. To do this, it is possible to use techniques of dehydration of alcohols, notably via molecular sieves, which are well known to a person skilled in the art.

The fermentation step c) thus allows the production of a stream of oxygenated compounds as described above, said stream, advantageously separated from the strain, comprising between 0.1% and 99.9% water and between 99.9% and 0.1% alcohols, diols and/or carboxylic acids and preferably between 30% and 98% water and between 2% and 70% alcohols, diols and/or carboxylic acids.

In a very preferred embodiment of the invention, said stream of oxygenated compounds separated out on conclusion of step d) is at least partly recycled into said catalytic pyrolysis step a).

In this preferred embodiment, the weight proportion of said stream comprising at least one oxygenated compound produced by a fermentation step and recycled into the catalytic pyrolysis step advantageously represents 0.01% to 20% and preferably 0.05% to 10% by weight relative to the mass of biomass introduced into the process according to the invention.

The recycling of said stream of oxygenated compounds allows the yield of BTX obtained to be improved relative to the prior art.

Moreover, the process according to the invention also allows the production of alcohol and preferably of ethanol from the portion of the stream of oxygenated compounds that is not recycled.

In the case where said stream of oxygenated compounds is recycled to the catalytic pyrolysis step, a supplement of oxygenated compounds preferably chosen from alcohols containing 2 to 6 carbon atoms chosen from ethanol, n-propanol, isopropanol, butanol, isobutanol and hexanol, diols containing 2 to 4 carbon atoms chosen from 2,3-butylene glycol (2,3-butanediol), acid alcohols containing 2 to 4 carbon atoms and preferably lactic acid, carboxylic acids containing 2 to 6 carbon atoms chosen from acetic acid, butyric acid and hexanoic acid, aldehydes containing 2 to 12 carbon atoms and preferably 2 to 6 carbon atoms, ketones containing 3 to 12 carbon atoms chosen from acetone and butanone, alone or as a mixture, and esters containing 2 to 12 carbon atoms and preferably 2 to 6 carbon atoms, may advantageously be optionally added in said catalytic pyrolysis step a).

Said stream of supplemental oxygenated compounds may advantageously come from any process external to the process according to the invention allowing production of streams of oxygenated compounds, for example hydration of olefins, hydrogenation of aldehydes, hydrogenation of acids and dicarboxylic acids or hydrogenation of sugars, etherification, oxidation of alcohols, carbonylation, transesterification, or oxidation of alcohols and hydrocarbons for the production of ketones.

According to another embodiment of the invention, no stream derived from the fermentation step c) is recycled into said catalytic pyrolysis step a), and preferably said stream of oxygenated compounds is not recycled into the catalytic pyrolysis step a).

Recycling step e)

In accordance with the invention, the process comprises a step e) of recycling at least part of said unreacted gaseous effluent derived from step d) into the catalytic pyrolysis step a). The unreacted gaseous effluent derived from step d) of separation of the fermentation stream advantageously comprises carbon monoxide and carbon dioxide and preferably a carbon monoxide content of between 0 and 40% by mass, preferably between 1% and 15% by mass and very preferably between 4% and 28% by mass and a carbon dioxide content of between 0 and 30% by mass, preferably between 1% and 29% by mass and very preferably between 2% and 20% by mass, the percentages being expressed as mass percentages relative to the total mass of the effluent.

The unreacted gaseous effluent derived from step d) of separation of the fermentation stream also advantageously comprises hydrogen, C1-C4 light gases, olefins and may also contain a small content of aromatic impurities, for instance benzene and toluene. The sum of the content of elements composing said effluent is equal to 100%.

Preferably, said unreacted gaseous effluent in the fermentation step which is separated out in step d) is recycled, preferably via a compressor, into the catalytic pyrolysis step a). This gaseous stream then serves as fluid for entraining the feed into said reactor.

Moreover, the unreacted uncondensable gaseous effluent in the fermentation step which is recycled into the catalytic pyrolysis step has a higher partial pressure of hydrocarbon than that in the prior art, which makes it possible to improve the production of BTX in the catalytic pyrolysis step.

BRIEF DESCRIPTION OF THE DRAWINGS

FIG. 1 illustrates the process according to the invention in the preferred embodiment in which the stream of oxygenated compounds produced in the fermentation step is recycled into the catalytic pyrolysis step.

In FIG. 1, the biomass is fed via pipe 1 into a fluidized-bed catalytic pyrolysis reactor A. A stream comprising at least one oxygenated compound is also fed via pipe 12 into the catalytic pyrolysis reactor. The gaseous effluent from catalytic pyrolysis is then sent via pipe 2 into a fractionation section B so as to recover an uncondensable gaseous effluent, comprising at least carbon monoxide (CO) and carbon dioxide ($CO_2$) via pipe 6, a liquid cut known as BTX via pipe 3, a heavy liquid cut predominantly comprising compounds having a number of carbon atoms greater than 9, via pipe 4 and water via pipe 5.

Flue gases are also withdrawn from the pyrolysis reactor via pipe 7.

All of the gaseous effluent comprising carbon monoxide (CO) and carbon dioxide ($CO_2$) is sent via pipe 6 into a fermentation step D producing a liquid fermentation stream comprising at least one stream comprising at least one oxygenated compound that is withdrawn via pipe 9. The fermentation step D also comprises separation of the liquid fermentation stream obtained into a stream comprising at least one oxygenated compound that is withdrawn via pipe 10, water withdrawn via pipe 8 and an uncondensable gaseous effluent comprising unreacted CO and $CO_2$, withdrawn via pipe 10. The gaseous effluent comprising unreacted CO and $CO_2$ is then recycled via a compressor C into the catalytic pyrolysis reactor A via pipe 11.

The invention is illustrated by the following examples, which are not in any way limiting.

Example 1: Catalytic Pyrolysis without Coupling to a Fermentation Process

Example 1 presents the case of catalytic pyrolysis of a variety of pine with a capacity of 2500 tonnes per day with a portion of the uncondensable gaseous effluent separated from the gaseous effluent from pyrolysis being recycled to the catalytic pyrolysis reactor. The biomass is fed into the catalytic pyrolysis reactor at a rate of 104 tonnes per hour. The recycle/biomass weight ratio is 1.5 so as to be in the desired hydrodynamic conditions.

In this example, the catalyst used is a commercial ZSM5 with a crystal content of 40%. The reactor is operated at a temperature of 580° C., at a pressure of 0.4 MPa abs. and at a catalytic WHSV of 0.3 $h^{-1}$.

Under these conditions, the yield of BTX is 15% by weight relative to the ash-free dry feed. The composition of the recycled gas is presented in the table below.

TABLE 1

Composition case of the recycled gas in the reference case
Under these conditions, the hydrocarbon concentration of the
stream returned to the pyrolysis reactor is about 14%, leading
to a partial pressure of hydrocarbon of about 0.7 bar absolute.

| Composition of the recycled gas | wt % |
| --- | --- |
| Hydrogen | 0.5% |
| CO | 50.0% |
| $CO_2$ | 35.4% |
| Methane | 7.3% |
| Ethane | 0.5% |
| Ethylene | 4.8% |
| Propane | 0.1% |
| Propylene | 1.3% |

Example 2: According to the Invention without Recycling of Oxygenated Compounds

Example 2 corresponds to the case of catalytic pyrolysis performed under the same operating conditions as those in Example 1, but for which the uncondensable gaseous effluent comprising CO and $CO_2$ is sent to a fermentation unit.

The gaseous effluent thus constitutes the feed for the fermentation step and corresponds to a mass flow rate of 192 tonnes per hour having the composition presented in Table 2.

TABLE 2

Composition of the gaseous effluent sent to the fermentation process

| Composition of the gaseous effluent sent to the fermentation process | wt % |
| --- | --- |
| Hydrogen | 1.0% |
| Carbon monoxide | 16.0% |
| Carbon dioxide | 62.3% |
| Methane | 13.0% |

TABLE 2-continued

Composition of the gaseous effluent sent to the fermentation process

| Composition of the gaseous effluent sent to the fermentation process | wt % |
|---|---|
| Ethane | 1.0% |
| Ethylene | 5.2% |
| Propane | 0.3% |
| Propylene | 1.3% |

The fermentation step is performed using a strain of *Clostridium ljungdahlii* specifically allowing the conversion of CO to ethanol under the following operating conditions: The percentage of CO contained in the gaseous substrate that is supplied to the fermentation process is 16% by weight and the growth medium of the microorganism is the PETC medium (American Type Culture Collection (ATCC) medium 1754).

The fermentation step is fed with the stream of gaseous substrate described above and is conducted at atmospheric pressure, with stirring at 300 rpm, at a temperature of 39° C., at a pH regulated between 5.5 and 6, and at a redox potential of −250 mV. It comprises a first phase of production of the microorganism through a chain of propagation leading to a sufficient quantity of microorganisms for inoculating the production reactors.

The production process results in the generation of a liquid fermentation stream separated from the strain extracted from the reactor, said fermentation liquid comprising 94% by weight of water, 5% by weight of ethanol and 1% by weight of residual acetic acid. The alcohols, mainly ethanol, contained in this stream are recovered by distillation, leading to an azeotropic cut comprising 95% of alcohols.

Thus, a total production of 16 tonnes of ethanol per hour is generated, i.e. about 15.4% by weight relative to the ash-free dry feed.

By virtue of the conversion of the CO, the composition of the recycled gas is enriched in hydrocarbons, as presented in Table 3.

TABLE 3

Composition of the recycled gas of Example 2

| Composition of the recycled gas | wt % |
|---|---|
| Hydrogen | 1.1% |
| CO | 7.9% |
| $CO_2$ | 68.3% |
| Methane | 14.2% |
| Ethane | 1.0% |
| Ethylene | 5.7% |
| Propane | 0.3% |
| Propylene | 1.4% |

Thus, the hydrocarbon concentration is about 23% by weight, leading to a partial pressure of hydrocarbon of about 1.3 bar absolute.

This increase in the partial pressure of hydrocarbon, which is favourable to aromatization in the pyrolysis reactor, makes it possible to obtain a BTX yield of 15.4% by weight, i.e. a 3% improvement in BTX production relative to the reference case, which, given the large capacity of the unit, is very significant.

Combination of the catalytic pyrolysis process and of the fermentation process for the production of ethanol thus makes it possible to upgrade the CO, generally intended to be flared off, as a high value-added product, namely ethanol, and to improve the performance of the catalytic pyrolysis process, this twofold effect very markedly improving the viability of the process relative to Example 1.

Example 3: According to the Invention with Partial Recycling of Alcohols

Example 3 is similar to Example 2, but, in addition, part of the ethanol generated by the fermentation process is recycled into the catalytic pyrolysis reactor.

Thus, 25% of the 16 tonnes of ethanol produced are recycled, i.e. 4 tonnes per hour. The proportion of ethanol recycled into the catalytic pyrolysis reactor thus represents about 4% by weight of the biomass introduced into said catalytic pyrolysis reactor.

This recycling makes it possible to obtain an improved BTX yield. Thus, a BTX yield of 16.5% by weight relative to the ash-free dry biomass is obtained, i.e. an increase of 11% by weight relative to the reference case. In addition to this increase in the BTX cut, about 12 tonnes of ethanol are generated, i.e. about 12% by weight relative to the ash-free dry biomass.

This particular embodiment of the invention makes it possible to increase the production of BTX and to generate a new upgradable alcohol cut. This arrangement also makes it possible to optimally adjust the selectivity of the BTX relative to the alcohol generated and to be as close as possible to the economic optimum.

The invention claimed is:

1. A process for producing BTX and alcohols from biomass, comprising at least the following steps:
   a) catalytic pyrolysis of said biomass in a fluidized-bed reactor producing a gaseous pyrolysis effluent,
   b) separation of said gaseous pyrolysis effluent into at least one BTX fraction and a gaseous effluent comprising at least carbon monoxide and carbon dioxide,
   c) sending all of the gaseous effluent comprising at least carbon monoxide and carbon dioxide derived from the separation step b) into a fermentation step producing a liquid fermentation stream comprising at least one stream comprising at least one oxygenated compound chosen from alcohols containing 2 to 6 carbon atoms, diols containing 2 to 4 carbon atoms, acid alcohols containing 2 to 4 carbon atoms, carboxylic acids containing 2 to 6 carbon atoms, aldehydes containing 2 to 12 carbon atoms, ketones containing 3 to 12 carbon atoms and esters containing 2 to 12 carbon atoms, alone or as a mixture,
   d) separating said fermentation stream obtained on conclusion of step c) into at least said stream comprising at least one oxygenated compound, an aqueous fraction and an unreacted gaseous effluent,
   e) recycling at least part of said unreacted gaseous effluent into the catalytic pyrolysis step a).

2. The process according to claim 1, in which the catalytic pyrolysis step a) takes place in the presence of a zeolite catalyst comprising at least one zeolite chosen from ZSM-5, ferrierite, zeolite beta, zeolite Y, mordenite, ZSM-23, ZSM-57, EU-1 and ZSM-11, whether or not doped with a metal chosen from iron, gallium, zinc and lanthanum.

3. The process according to claim 1, in which the catalytic pyrolysis step a) is performed at a temperature of between 400 and 1000° C., at an absolute pressure of between 0.1 and 0.5 MPa and at a WHSV of between 0.01 and 10 h$^{-1}$.

4. The process according to claim 1, in which said fermentation step c) is performed in the presence of at least one microorganism chosen from the following microorganisms: *Acetogenium kivui, Acetoanaerobium noterae, Acetobacterium woodii, Alkalibaculum bacchi* CP11 (ATCC BAA-1772), *Blautia producta, Butyribacterium methylotrophicum, Caldanaerobacter subterraneous, Caldanaerobacter pacificus subterraneous, hydrogenoformans Carboxydothermus, Clostridium aceticum, Clostridium acetobutylicum, Clostridium acetobutylicum* P262 (DSM 19630 from DSMZ Germany), *Clostridium autoethanogenum* (DSM 19630 from DSMZ Germany), *Clostridium autoethanogenum* (DSM 10061 from DSMZ Germany), *Clostridium autoethanogenum* (DSM 23693 from DSMZ Germany), *Clostridium autoethanogenum* (DSM 24138 from DSMZ Germany), *Clostridium carboxidivorans* P7 (ATCC PTA-7827), *Clostridium coskatii* (ATCC PTA-10522), *Clostridium drakei, Clostridium ljungdahlii* PETC (ATCC 49587), *Clostridium* ER12 *ljungdahlii* (ATCC 55380), *Clostridium ljungdahlii* C-01 (ATCC 55988), *Clostridium ljungdahlii* 0-52 (ATCC 55889), *Clostridium magnum, Clostridium pasteurianum* (DSM 525 from DSMZ Germany), *Clostridium ragsdali* P11 (ATCC BAA-622), *Clostridium scatologenes, Clostridium thermoaceticum, Clostridium ultunense, Desulfotomaculum kuznetsovii, Eubacterium limosum, sulfurreducens Geobacter, Methanosarcina acetivorans, Methanosarcina barken, Morrella thermoacetica, Morrella thermoautotrophica, Oxobacter pfennigii, Peptostreptococcus productus, Ruminococcus productus, Thermoanaerobacter kivui*, and mixtures thereof.

5. The process according to claim 4, in which the microorganisms are chosen from *Clostridium autoethanogenum, Clostridium ljungdahlii, Clostridium aceticum, Morella thermoacetica, Acetobacterium woodii* and *Alkalibaculum bacchi* for producing ethanol and/or acetate, *Clostridium autoethanogenum, Clostridium ljungdahlii* and *C. ragdalei* for producing 2,3-butanediol and *Clostridium carboxidivorans, Clostridium drakei, Clostridium scatologenes* and *Butyribacterium methylotrophicum* for producing butyrate and butanol; and mixtures thereof.

6. The process according to claim 1, in which said fermentation step c) is performed at a growth temperature of between 20 and 80° C., at an absolute pressure of between 0.1 and 0.4 MPa and at a pH of between 3 and 9.

7. The process according to claim 1, in which the alcohols containing 2 to 6 carbon atoms are chosen from ethanol, n-propanol, isopropanol, butanol, isobutanol and hexanol, the diols containing 2 to 4 carbon atoms are chosen from 2,3-butylene glycol (2,3-butanediol), the acid alcohol containing 2 to 4 carbon atoms is lactic acid, the carboxylic acids containing 2 to 6 carbon atoms are chosen from acetic acid, butyric acid and hexanoic acid, the aldehydes containing 2 to 12 carbon atoms are chosen from ethanal, propanal, butanal, pentanal, 3-methylbutanal, hexanal, furfural and glyoxal, alone or as a mixture, the ketones containing 3 to 12 carbon atoms are chosen from acetone, butanone, cyclohexanone, acetophenone and acetylacetone, alone or as a mixture, and the esters containing 2 to 12 carbon atoms are chosen from methyl formate, methyl acetate, methyl propionate, methyl butanoate, methyl pentanoate, ethyl acetate, propyl acetate, isopropyl acetate, butyl acetate, isobutyl acetate and butyl butyrate, alone or as a mixture.

8. The process according to claim 6, in which the stream comprising at least one oxygenated compound comprises ethanol, n-propanol, isopropanol, butanol, isobutanol, hexanol, acetic acid, butyric acid, hexanoic acid, lactic acid, acetone, butanone or 2,3-butylene glycol (2,3-butanediol), alone or as a mixture.

9. The process according to claim 1, in which a hydrogen supplement is introduced into said fermentation step c).

10. The process according to claim 1, in which the separation step d) is performed by steam originating from the catalytic pyrolysis step.

11. The process according to claim 1, in which said stream of oxygenated compounds separated out on conclusion of step d) is at least partly recycled into said catalytic pyrolysis step a).

12. The process according to claim 10, in which a supplement of oxygenated compounds chosen from alcohols containing 2 to 6 carbon atoms chosen from ethanol, n-propanol, isopropanol, butanol, isobutanol and hexanol, diols containing 2 to 4 carbon atoms chosen from 2,3-butylene glycol (2,3-butanediol), lactic acid, carboxylic acids containing 2 to 6 carbon atoms chosen from acetic acid, butyric acid and hexanoic acid, aldehydes containing 2 to 12 carbon atoms and ketones containing 3 to 6 carbon atoms chosen from acetone and butanone, alone or as a mixture, and esters containing 2 to 12 carbon atoms, are added in said catalytic pyrolysis step a).

13. The process according to claim 1, in which said stream of oxygenated compounds separated out on conclusion of step d) is not recycled into the catalytic pyrolysis step a).

14. The process according to claim 1, wherein in step e) all of said unreacted gaseous effluent is recycled into the catalytic pyrolysis step a).

* * * * *